US011331077B2

(12) United States Patent
Dhatt

(10) Patent No.: US 11,331,077 B2
(45) Date of Patent: *May 17, 2022

(54) TOUCHLESS INPUT ULTRASOUND CONTROL

(71) Applicant: FUJIFILM SONOSITE, INC., Bothell, WA (US)

(72) Inventor: Davinder S. Dhatt, Bothell, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/103,599

(22) Filed: Nov. 24, 2020

(65) Prior Publication Data

US 2021/0204912 A1 Jul. 8, 2021

Related U.S. Application Data

(63) Continuation of application No. 16/206,806, filed on Nov. 30, 2018, now Pat. No. 10,863,971.

(51) Int. Cl.

| | |
|---|---|
| ***A61B 8/00*** | (2006.01) |
| ***G06F 3/16*** | (2006.01) |
| ***G06K 9/00*** | (2022.01) |
| ***G06N 3/04*** | (2006.01) |
| ***G06N 3/08*** | (2006.01) |

(52) U.S. Cl.

CPC .............. *A61B 8/467* (2013.01); *A61B 8/468* (2013.01); *A61B 8/54* (2013.01); *G06F 3/167* (2013.01); *G06K 9/00315* (2013.01); *G06K 9/00335* (2013.01); *G06N 3/04* (2013.01); *G06N 3/08* (2013.01)

(58) Field of Classification Search

CPC combination set(s) only.
See application file for complete search history.

(56) References Cited

U.S. PATENT DOCUMENTS

| | | | | |
|---|---|---|---|---|
| 9,730,671 | B2 | 8/2017 | Gering | |
| 2014/0214424 | A1 | 7/2014 | Wang et al. | |
| 2014/0358002 | A1* | 12/2014 | Daoura | A61B 8/0883 600/443 |

(Continued)

FOREIGN PATENT DOCUMENTS

| | | | |
|---|---|---|---|
| JP | 2011104066 | A | 6/2011 |
| KR | 1020080046199 | A | 5/2008 |
| KR | 1020090097292 | A | 9/2009 |

OTHER PUBLICATIONS

Korean Search Report for Application No. PCT/US2019/061571 dated Mar. 2, 2020, 2 pages.

(Continued)

*Primary Examiner* — Deeprose Subedi

(74) *Attorney, Agent, or Firm* — Womble Bond Dickinson (US) LLP

(57) ABSTRACT

A method and apparatus are disclosed herein for controlling an ultrasound machine using one or more touchless inputs. In one embodiment, the method for controlling operation of the ultrasound machine comprises obtaining one or more touchless inputs; determining one or more operations to control the ultrasound machine based on the one or more touchless inputs and machine state of the ultrasound machine; and controlling the ultrasound machine using the one or more operations.

20 Claims, 6 Drawing Sheets

Perform lip reading (including capturing lip movements with one or more cameras)
101

Determine operations (e.g., adjust gain, adjust depth, freeze image, save an image, add/move annotations, create a report, etc.) to control an ultrasound machine based on one or more touchless inputs (e.g., results of lip reading recognition, one or more of captured audio, ultrasound image information, examination type, work flow, expected user operation, etc.) and the machine state of the ultrasound machine.
102

Generate and display one or more operations (e.g., commands) to be performed from which the user selects and/or confirms (optional)
103

Control the ultrasound machine using the operations (in response to selection/confirmation, if necessary)
104

(56) References Cited

U.S. PATENT DOCUMENTS

| | | | |
|---|---|---|---|
| 2017/0071573 | A1 | 3/2017 | Takahashi |
| 2018/0268812 | A1 | 9/2018 | Kim et al. |
| 2019/0336107 | A1 | 11/2019 | Hope Simpson et al. |

OTHER PUBLICATIONS

International Preliminary Report and Written Opinion on the Patentability of Application No. PCT/US2019/061574 dated Jun. 10, 2021, 9 pages.

* cited by examiner

TOUCHLESS INPUT ULTRASOUND CONTROL

RELATED APPLICATION

The present application is a continuation of and claims the benefit of U.S. patent application Ser. No. 16/206,806, filed on Nov. 30, 2018 and entitled "TOUCHLESS INPUT ULTRASOUND CONTROL", and which is incorporated by reference in its entirety.

FIELD OF THE INVENTION

One or more exemplary embodiments relate to an ultrasound machine and a method of operating the same, and more particularly, to an ultrasound machine that uses lip reading to generate, at least in part, operations to control an ultrasound machine.

BACKGROUND OF THE INVENTION

Ultrasound systems radiate an ultrasonic signal generated from an ultrasound probe into an object, such as a patient, and receive an echo signal reflected from the internal part of the object. An image of the internal part of the object is generated using received echo signals. More specifically, ultrasound diagnostic machines generate an ultrasound image by using ultrasonic image data acquired from an ultrasound probe and display the generated ultrasound image on a screen to provide the ultrasound image to a user. The ultrasound machine may include a control panel for controlling the ultrasound machine and setting various functions.

In general, ultrasound machines have multiple functional keys for receiving user input and an input device, such as a keyboard, that are part of a control panel. In order for the user to control an ultrasound system including an ultrasound probe, various input units on the control panel have to be manipulated by a user, which causes inconvenience when using the ultrasound system. In particular, when a clinician performs a diagnosis of a patient by using the ultrasound probe, it may be inconvenient for a user to manipulate the control panel that is spaced apart from the user and that takes a long time to manipulate.

Furthermore, clinicians often need to adjust the ultrasound machine during sterile procedures. However, they cannot easily do so because they are working in a sterile field with an ultrasound machine that is not sterile and touching it would break sterility. Also, both hands are often engaged, one to hold the probe and one to hold an instrument such as a needle for injection or biopsy, such that there is no spare hand to reach to the machine controls. The clinician often deals with this by having a nurse or assistant adjust the machine for them, but this is inefficient and not always possible. The clinician sometimes uses a sterile device such as a cotton swab to adjust the ultrasound machine, but this is awkward and requires disposal of the swab with each adjustment (as the dirty swab should not be returned to sterile field).

Some ultrasound machines use voice control of the ultrasound machine to deal with this issue. Generally, this does not work well because a hospital tends to be a very noisy space and it is difficult for the voice control to pick out commands from the background noise or other conversations. This is particularly important in a hospital setting because the user definitely does not want the ultrasound machine to change state when not specifically commanded, especially at a critical time in the procedure.

Some ultrasound machines have buttons on the probe to control the ultrasound machine. These can be awkward to use because of the different grip positions that are required with the buttons being present and the fact that the probe may be covered by a sterile sheath.

SUMMARY OF THE INVENTION

A method and an apparatus are disclosed herein for controlling an ultrasound machine using one or more touchless inputs. In one embodiment, the method for controlling operation of the ultrasound machine comprises obtaining one or more touchless inputs; determining one or more operations to control the ultrasound machine based on the one or more touchless inputs and machine state of the ultrasound machine; and controlling the ultrasound machine using at least one of the one or more operations.

BRIEF DESCRIPTION OF THE DRAWINGS

The present invention will be understood more fully from the detailed description given below and from the accompanying drawings of various embodiments of the invention, which, however, should not be taken to limit the invention to the specific embodiments, but are for explanation and understanding only.

DETAILED DESCRIPTION

In the following description, numerous details are set forth to provide a more thorough explanation of the present invention. It will be apparent, however, to one skilled in the art, that the present invention may be practiced without these specific details. In other instances, well-known structures and devices are shown in block diagram form, rather than in detail, in order to avoid obscuring the present invention.

Methods and apparatuses for generating commands to control an ultrasound machine using lip reading and machine state information of the ultrasound machine are disclosed. The use of lip reading for controlling an ultrasound machine enables hands-free operation, which is very advantageous, particularly in sterile medical environments. In one embodiment, the commands are determined using touchless commands. The touchless commands may be identified using video image and/or audio. In one embodiment, the touchless commands comprise a combination of lip reading and additional information, such as, but not limited to, one or more the examination type being performed with the ultrasound machine, features from an ultrasound image, expectations of what the user may do next with the ultrasound machine, etc. In one embodiment, the commands are determined using a command generator that includes a neural network (e.g., a deep learning neural network) or other artificial intelligence functionality.

Figure 1:
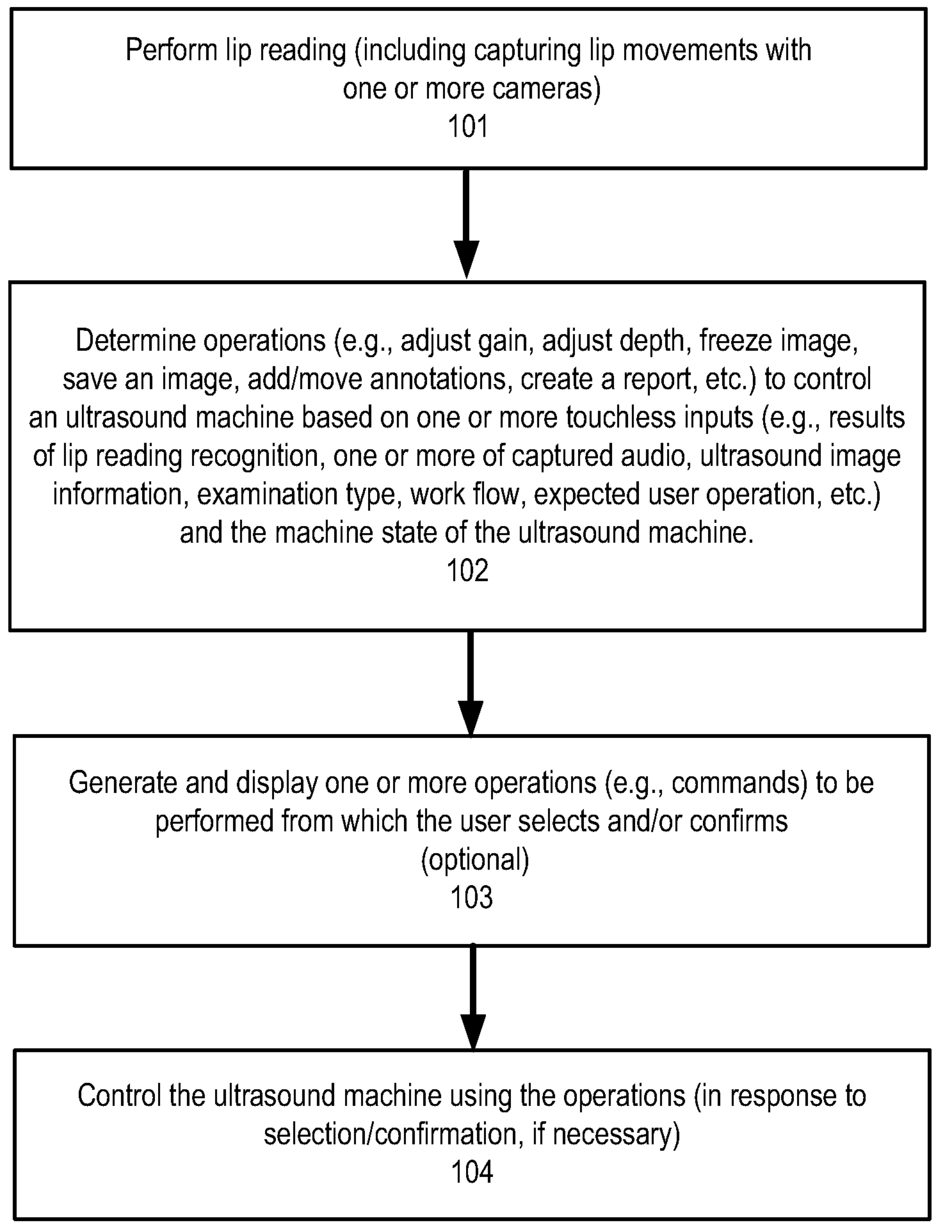
FIG. 1 is a flow diagram of one embodiment of a process for controlling an ultrasound machine using touchless inputs.

FIG. 1 is a flow diagram of one embodiment of a process for controlling an ultrasound machine using touchless inputs. The process is performed by processing logic that may comprise hardware (circuitry, dedicated logic, etc.), software (such as is run on a general-purpose computer system or a dedicated machine), firmware, or a combination of the three.

Referring to FIG. 1, the process begins by performing lip reading, which includes capturing lip movements with one or more cameras and performing lip recognition on those lip movements (processing block 101). There are a number of techniques to perform lip reading by capturing images of lips, analyzing the images (e.g., measure the height and width of the lips from images captured by a camera as well as other features such as the shape of the ellipse bounding the lips, etc.) to determine the movement of the lips, recognizes a sequence of shapes formed by the mouth and then matching them to a specific word or sequence of words. In one embodiment, the lip reading is performed using a neural network (e.g., a deep learning neural network).

Next, processing logic determines operations to control an ultrasound machine based on one or more touchless inputs and machine state information of the ultrasound machine (processing block 102). In one embodiment, the operations are determined using a command generator of an ultrasound machine. In one embodiment, the command generator is implemented with processing logic that may comprise hardware (circuitry, dedicated logic, etc.), software (such as is run on a general-purpose computer system or a dedicated machine), firmware, or a combination of the three.

In one embodiment, the command generator receives various inputs and determines the commands based on these inputs. In one embodiment, the command generator includes a recognizer, or recognition engine, that performs one or more recognition routines on the input data to generate recognition results upon which it determines which of the commands that the user wants or is going to want to be performed. In one embodiment, the command generator uses a neural network (e.g., a deep learning neural network) as part of the process of determining the operations to be performed by the ultrasound machine. One such embodiment is described in more detail below.

In one embodiment, the generated operations include commands to control operating parameters such as, for example, but not limited to, adjusting gain (e.g., increasing gain, decreasing gain) and adjusting depth (e.g., increasing depth, decreasing depth). Other operating parameters such as transducer selection, turning on/off a mode (e.g., A-mode, B-mode or 2D mode, B-flow, C-mode, M-mode, Doppler mode (e.g., Color Doppler, Continuous wave (CW) Doppler, Pulsed wave (PW) Doppler, Duplex, Triplex, etc.), Pulse inversion mode, Harmonic mode, etc.), etc., could also be generated.

In one embodiment, the operations include freezing an ultrasound image being displayed by the ultrasound machine, saving an image being displayed by the ultrasound machine, adding to and/or moving an annotation (e.g., a label) or pictogram on an image being displayed by the ultrasound machine, and creating or filling in a report (e.g., a billing record, medical report, etc.) using information that is stored on or received by the ultrasound machine.

In one embodiment, the one or more touchless input comprises the results of lip reading recognition, captured audio information, image information of an ultrasound image being displayed by the ultrasound machine, an examination type for the examination being performed by an individual using the ultrasound machine, a list of operations (e.g., a workflow) being performed by the user of the ultrasound machine, and/or a next action to be performed by the user of the ultrasound machine. In one embodiment, one or more of such inputs are included in state information fed back from an ultrasound control subsystem of the ultrasound machine for use in command generation.

In one embodiment, the ultrasound system uses results of lip reading recognition combined with speech data to improve the accuracy of the control. In one embodiment, audio (e.g., a user's voice) is captured with a microphone and the captured audio is recognized for use in combination with the results of lip reading recognition in determining an operating parameter to change or other operation that the user wants performed. In one embodiment, the audio is spoken by the user of the ultrasound machine. Thus, in this manner, both audio and image recognition associated with a user mouthing a command are used to determine the operating parameter to adjust or another operation that the user wants to perform.

In one embodiment, the selection of the inputs (e.g., touchless inputs) to use or the impact of all these inputs for command determination changes based on one or more factors. These factors may be environmental factors or other information obtained about the environment (e.g., sensed from the environment). For example, in one embodiment, the outputs from lip reading recognition and audio recognition are weighted such that each does not have the same impact or contribution on the determination of the operation being identified based on information about the environment. In one embodiment, based on the noise in the environment, the system determines the operation that the user wants to perform based more heavily on the results of lip reading operation than the results of the audio recognition, or vice versa. In one embodiment, this is accomplished by dynamically adjusting the weights on outputs from lip reading recognition and audio recognition. Therefore, if the environment is determined to be too noisy (e.g., the noise level is above a threshold), then the results of the lip reading recognition may be weighted higher than the results of the audio recognition (or even exclusively used) when determining the operation that the user wants to perform.

In one embodiment, the ultrasound system ignores touchless inputs to the ultrasound system until it undergoes activation mode when it is activated to accept touchless inputs. Until the ultrasound system undergoes activation mode, the ultrasound system determines the user is looking directly into the camera. In this case, the ultrasound system ignores any speech utterances unless the user was looking directly into the camera when they were spoken. This would not present any real limitation to the clinician since they are typically looking at the machine when they are making adjustments that are based on commands. In another embodiment, the activation mode of the ultrasound system requires a gesture such as, for example, a facial cue to begin listening to speech utterances and/or studying visual data for lip reading. Examples of such a facial cue include, but are not limited to, closing both eyes for a certain predetermined period of time (i.e., a long blink), winking, nodding, etc.

Note that other data such as examination type, worklist, system log-in information, or other state information that is stored and available in the ultrasound machine may be used by the lip reading recognition routine to determine an operation that the user wants to perform. Similarly, image information associated with an image being displayed by the ultrasound machine may also be used by the lip reading recognition routine to determine an operation that the user wants to perform.

After determining one or more operations based on the results of lip reading recognition and the machine state of the ultrasound machine, in one embodiment, processing logic generates and causes to be displayed one or more user selectable operations that can be performed by the ultrasound machine (processing block 103). This starts a confirmation mode process that enables the user to select and/or confirm the operation that the ultrasound machine is going to perform. This may be particularly advantageous in situations where the command generator cannot ascertain with certainty what operation the user wants performed. The uncertainty may be due to the lip reading recognition results being less than 100% confident in its determination, due to some other recognition (e.g., audio recognition) results being less than 100% confident in its determination, and/or due to some other limitation in the accuracy of the inputs used in the command generation process (e.g., a mismatch between the command based on audio and the command based on the lip reading, etc.).

In one embodiment, the selectable operations are presented on the display and/or using audio (e.g., computer generated speech) of the ultrasound machine under control of its ultrasound imaging subsystem. In one embodiment, the selectable operations are presented in a list according to their likeliness (e.g., confidence) in matching the user's desired operation as determined by the command generator of the ultrasound machine. In one embodiment, the list of selectable operations includes a confidence factor generated by the command generator for each operation or other information to provide the user with an indication of the level of confidence associated with the determination of the operation by the ultrasound machine.

Note that presentation and/or confirmation operations are optional and not required. In an alternative embodiment, a single operation is determined and the command generated for performance by the ultrasound machine without selection and/or confirmation.

Next, in one embodiment, processing logic controls the ultrasound machine using the operations generated based on lip reading and control state information (processing block 104). In another embodiment, the operations are also generated based on audio information. In one embodiment, the control is implemented in response to a selection and/or confirmation of the operations, if necessary. In one embodiment, the control is performed by a control subsystem of the ultrasound machine.

Figure 2:
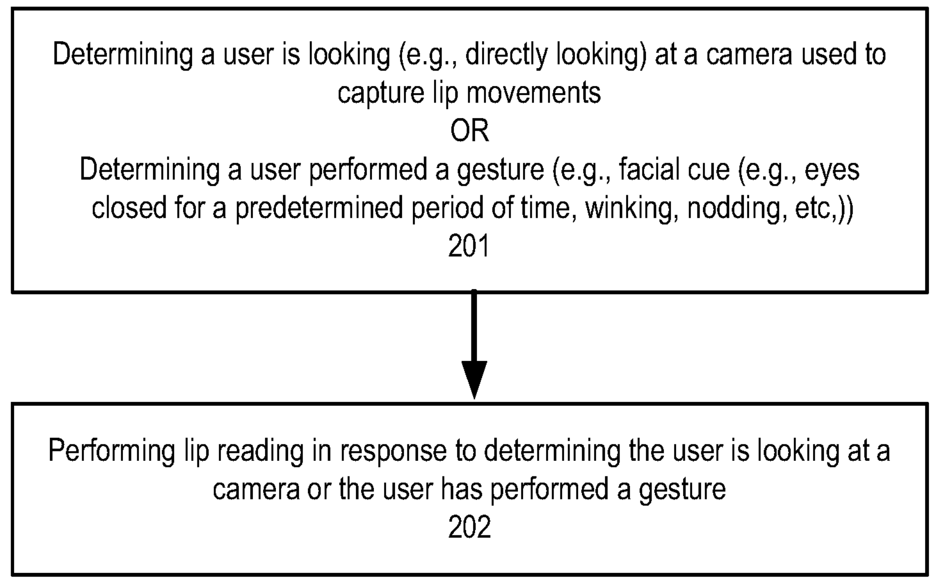
FIG. 2 is a flow diagram of one embodiment of a process for triggering the lip reading.

As set forth above, the determination of commands is based on performing lip reading and the recognition of lip movements. In one embodiment, the lip reading process is triggered in response to an activation mode, where the activation mode involves the occurrence of one or more operations. In one embodiment, one of the operations is a determination that the user is looking at the camera when speaking or lipping a command to be performed by the ultrasound machine. In another embodiment, the lip movement recognition occurs in response to the user performing a gesture that is recognized by the ultrasound machine. In one embodiment, the gesture comprises performance of a facial cue. In one embodiment, the facial cue comprises the eyes being closed by the user for a predetermined period of time, winking by the user, nodding by the user, or any other facial gesture. FIG. 2 is a flow diagram of one embodiment of a process for triggering the lip reading performed above. In one embodiment, the process is performed by a recognizer or recognition engine of a command generator of the ultrasound machine.

Referring to FIG. 2, the process begins by determining a user from which to receive touchless commands (processing block 201). In one or more embodiments, this determination is made by at least one of the following: determining a user is looking (e.g., directly looking) at a camera, determining the user performed a gesture, and through the use of a user identification or authentication process.

Determining a user is looking (e.g., directly looking) at a camera or determining the user performed a gesture requires image data from a camera. Such a camera may be on or embedded in the system, located on the probe of the ultrasound system, or attached to the ultrasound system. In one embodiment, the ultrasound machine determines the user is looking at a camera using eye tracking. The eye tracking uses a camera to record movements of the eyes and processes those images to determine where the user is gazing in a manner well-known in the art. In one embodiment, the camera used for performing eye tracking is a camera that is also used to capture lip movements for the purposes of lip reading, though a separate camera may be used. In one embodiment, the eye tracking is augmented to enable the system to determine which individual in the examination area to track. In one embodiment, this augmentation includes determining the orientation of face, facial recognition based upon the person who started an examination, and/or accessing information from a worklist that indicates a sonographer, physician, or other healthcare practitioner that is to be using the ultrasound machine for the examination. Note that more than one user of the ultrasound machine for the same examination may be identified in this manner.

In one embodiment, if an identified physician is a neonatologist, the settings of the ultrasound system are optimized for visualizing small anatomy as would be common in typical neonatal examinations. In one embodiment, after the examination has started, the identity of the physician is used as part of the machine learning process to more accurately predict the settings that the clinician or user may be seeking to adjust. Initial system settings are also determined using a profile associated with a user login.

In one embodiment, the determination of whether the user performed a gesture to trigger the lip reading recognition process is based on a facial cue or other wake gesture such as, for instance, but not limited to, closing their eyes for a predetermined period of time (i.e., a long blink), winking, nodding, etc., performed by the user.

In response to either determining the user is looking at a camera or determining the user performed a gesture, processing logic performs lip reading (processing block 202) and the remainder of the command generation process as described herein.

In an alternative embodiment, the system performs facial recognition or some other user identification/authentication process on the individual and only responds to the commands from the face of the individual that initiated the examination. That is, the system identifies the individual from perhaps a group of individuals located in proximity to the system. This is done using a user identification operation (e.g., facial recognition, obtaining ultrasound data such as a worklist or other information identifying the individual that is giving the examination, etc.).

After determining a user is looking (e.g., directly looking) at a camera, determining the user performed a gesture, and through the use of a user identification/authentication process, the system provides control of the ultrasound machine through use of touchless inputs to the identified individual. In other words, the system allows that individual to provide control the system using their touchless inputs.

In one embodiment, once the ultrasound system determines the individual(s) from which it will accept touchless commands for a particular examination, the ultrasound system does not accept touchless commands from other individuals that may be present at the examination.

Figure 3:
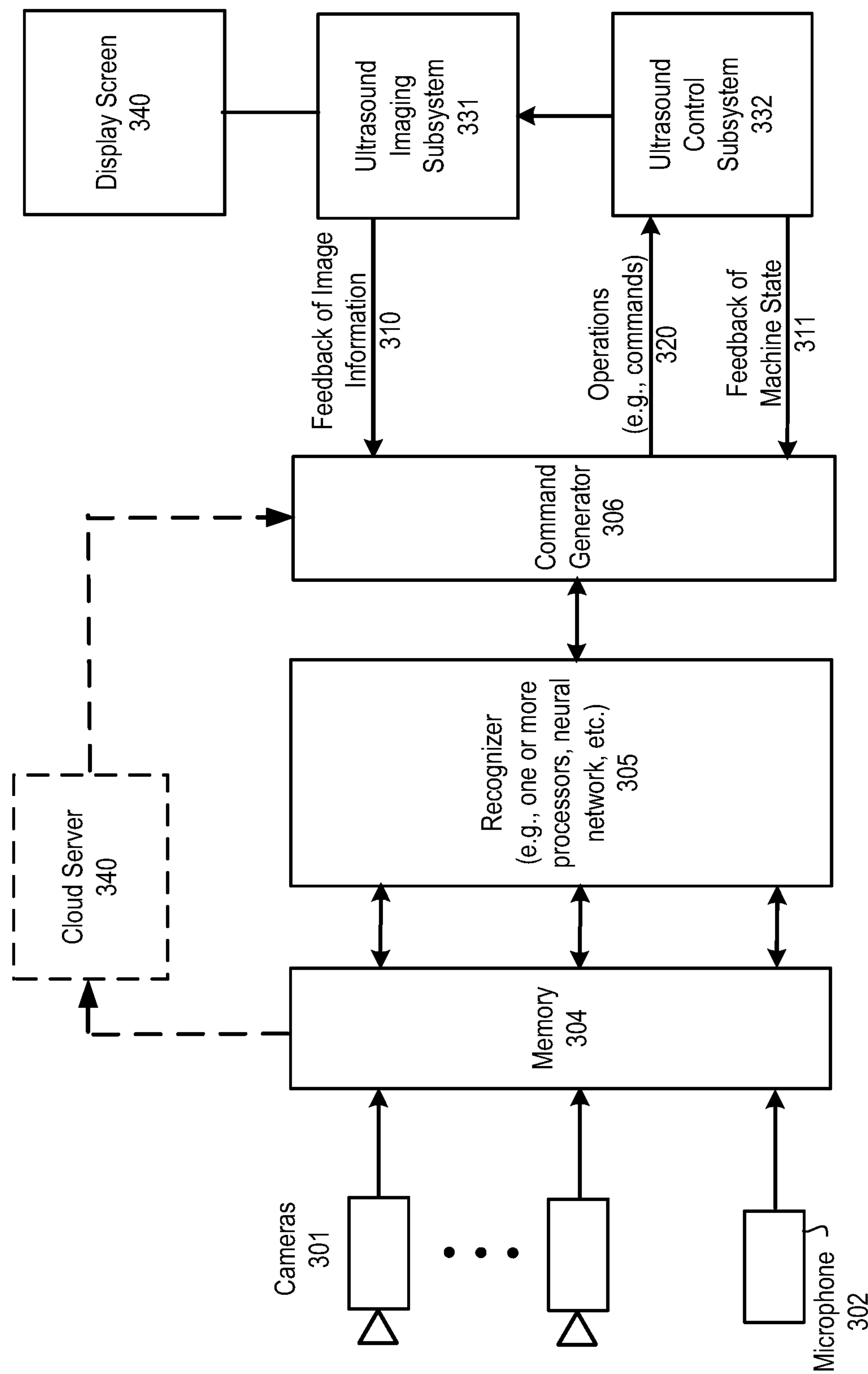
FIG. 3 is a block diagram of one embodiment of an ultrasound system having a command generator.

FIG. 3 is a block diagram of one embodiment of an ultrasound system having a command generator as discussed above. In one embodiment, the ultrasound machine includes a transducer probe to send and receive the sound waves (echoes) in a manner well-known in the art, which are processed to produce ultrasound images. The transducer probe has not been shown in FIG. 3 to avoid obscuring the techniques disclosed herein.

Referring to FIG. 3, ultrasound control subsystem 332 includes one or more processors. One processor causes electrical currents to be sent to the transducer probe to emit sound waves and also receives the electrical pulses from the probe that were created from the returning echoes. The processor processes the raw data associated with the received electrical pulses and forms an image. The processor sends the image data to ultrasound imaging subsystem 332, which displays the image on display 340. Thus, display screen 340 displays ultrasound images from the ultrasound data processed by the processor of ultrasound control subsystem 332.

The ultrasound system of FIG. 3 also includes one or more cameras 301 to capture images or video information that is stored in memory 304. In an alternative embodiment, microphone 302 records audio information that is also stored in memory 304. In one embodiment, one or more other non-audio inputs may be received by command generator 306. In one embodiment, these other non-audio inputs comprise one or more of feedback of image information 310 from ultrasound imaging system 331 of the ultrasound machine and feedback of machine state 311 from ultrasound control subsystem 332 of the ultrasound machine. In one embodiment, other non-audio input data includes workflow information for a given user or for a given type of procedure or examination for use in predicting or assisting in predicting next commands or steps in the examination or procedure. These may also be stored in memory 304. While memory 304 is shown as a single block of storage in FIG. 3, in an alternative embodiment, the data from cameras 301, microphone 302 and the non-audio inputs 303 are stored in more than one memory. In an additional alternative embodiment, the data is streamed directly, via a network communication interface, to a processor in the cloud or local server (e.g., cloud server 340) that is performing the operations described herein. In an alternative embodiment, the data is sent directly to a neural network (e.g., a deep learning neural network, etc.) for processing.

Command generator 306 accesses memory 304 and, in response thereto, generates one or more operations (e.g., commands) 320 for controlling the ultrasound machine. In one embodiment, command generator 306 is integrated into the ultrasound machine. In another embodiment, command generator 306 is a stand-alone device that may be coupled, via wired and/or wireless connection, to the ultrasound machine. In yet another embodiment, command generator 306 is part of a cloud-based computer resource that may be coupled, via wired and/or wireless connection, to the ultrasound machine.

In one embodiment, command generator 306 includes one or more processors, neural networks (e.g., a deep learning neural network, etc.), etc., to control the operation of ultrasound system through generation of control options or operations.

In one embodiment, command generator 306 includes recognizer, or recognition engine, 305 that performs recognition on the image data and audio data captured by cameras 301 and microphone 302, respectively, as part of generating the operations. For example, recognizer 305 accesses memory 304 for captured image information from one or more cameras 301 and performs lip reading recognition on lip movements captured by cameras 301 to determine a specific command from the individual that is using the ultrasound machine. For instance, the user may have lipped the command to increase the gain on the image being displayed by ultrasound imaging subsystem 331. The command is recognized by recognizer 305, and, in response thereto, command generator 306 accesses the current gain value that is provided in machine state information 311 and generates a command to increase the gain of the ultrasound machine from its current value to an increased value. In one embodiment, the gain increase is a preset amount. In another embodiment, the command provided by the user includes an amount of parameter change that is desired "increase gain by 10%"). In another embodiment, the gain increase that occurs when performing the command is specified by the user and is recognized by recognizer 305. In yet another embodiment, due to network machine learning image recognition features, an optimization delta is identified and the correct amount of gain is applied, such that the ultrasound image being displayed is optimized. After generating the command, the command is sent to ultrasound control subsystem 332 which controls ultrasound imaging subsystem 331 and causes the gain of the image being displayed by ultrasound imaging subsystem 331 to be increased. In one embodiment, the same process is performed to decrease the gain, increase or decrease the depth, or control any other operating parameter.

In the case of freezing the image being displayed by the ultrasound imaging subsystem 331, the lip movements specifying the command are recognized by recognizer 305, and, in response thereto, command generator 306 generates a command to ultrasound control subsystem 332 to signal ultrasound imaging subsystem 331 to freeze the image being displayed on display screen 340. Note that freezing an ultrasound image may be part of a process to save an ultrasound image.

In the case of saving the image being displayed by ultrasound imaging subsystem 331, the lip movements specifying the command are recognized by recognizer 305, and, in response thereto, command generator 306 generates a command to ultrasound control subsystem 332 to signal ultrasound imaging subsystem 331 to save the image being displayed on display screen 340. Note that in one embodiment, the image data that is displayed by ultrasound imaging subsystem 331 is from ultrasound control subsystem 332. Therefore, in response to a command to ultrasound control subsystem 332 to save the image being displayed on display screen 340, ultrasound control subsystem 332 stores the image data for the image being displayed on display screen 340 in a memory (e.g., memory 304).

In one embodiment, the command is recognized by recognizer 305, and, in response thereto, command generator 306 also accesses historical, workflow and/or examination data that is provided in machine state information 311 and generates a command. For example, the user or physician may have a habit of freezing or saving an image frame after adjusting the depth of the image. Using the identity of the clinician or user, as for example described above, an instruction or command can be automatically implemented to save or freeze an image after a command was given to change the depth of the image, thereby combining the optimization delta with historical data. Historical data is not limited to actions performed solely by one particular clinician (i.e., an individual) and may be the actions of a group of individuals (e.g., other clinicians, physicians, individuals at medical facilities, etc.). Furthermore, historical data can include previously used settings, parameters, and/or configurations of the system, data learned by the system or other systems (e.g., data from machine learning or artificial intelligence processes, etc.), etc.

In the case of an annotation, recognizer 305 recognizes the lip movements as a command by the user to generate an annotation to be placed on an image being displayed by ultrasound imaging subsystem 331. In one embodiment, the lip movements recognized by command generator 306 not only include the command to add an annotation to the image being displayed by imaging subsystem 331, but also include the actual annotation. Note that a combination of two or more touchless inputs (e.g., lip reading and speech) may be used together to increase the accuracy of the dictation recognition. In one embodiment, the starting and ending of the annotation are also recognized by recognizer 305. In one embodiment, recognizer 305 determines the starting and ending of the annotation by recognizing start and stop words being lipped by the user. In an alternative embodiment, the recognizer 305 recognizes one or more gestures (e.g., a facial cue) made by the user to indicate the start and stop of the annotation.

In one embodiment, recognizer 305 also recognizes commands lipped by the user to move an annotation that is being displayed by the ultrasound imaging subsystem 331 on the display. In one embodiment, recognizer 305 recognizes lip movements indicating one or more commands to move the annotation up, down, left, and right on the image being displayed.

In one embodiment, recognizer 305 also recognizes lip movements to generate a command to create a report. In one embodiment, the report may be a billing record that is created and includes a predetermined set of information that is necessary to ensure the bill is processed and paid. In another embodiment, the report includes a medical record report that includes the information from the ultrasound examination being performed. In one embodiment, the report creation includes dictating notes into the report. In one embodiment, the dictation of notes is performed by having image of the report displayed on display screen 340 by ultrasound image subsystem 331 and directing the ultrasound control subsystem to direct recognizer 305 recognizing lip movements, using recognizer 305, to indicate one or more commands to move the notes up, down, left, and right on the image being displayed to a specific location(s) in the report. Also, in one embodiment, recognizer 305 determines the starting and ending of the dictated notes by recognizing start and stop words being lipped by the user.

In one embodiment, command generator 306 generates operations 320 (e.g., increase gain, decrease gain, increase depth, decrease depth, freeze image, save image, etc.) in response to recognition results and information received from other portions of the ultrasound machine. In one embodiment, the feedback includes feedback of machine state information 301 from the ultrasound control subsystem 332. In another embodiment, the feedback includes feedback of image information 310 from the ultrasound imaging subsystem 331. The image information may correspond to the image being displayed on display screen 340. This information may be used to determine the operation that the user wants to perform. For example, the ultrasound system may be able to determine a feature that the user is likely interested in viewing based on the worklist or examination type specified in control state information 311. Based on the appearance of that feature in the image, the ultrasound system is able to use the information to bias the command that is being generated based on results of the lip reading. That is, the results of the lip reading are impacted by an image feature or other image information that is in the ultrasound system.

In one embodiment, the ultrasound system also has one or more user input devices (e.g., a keyboard, cursor control device, etc.) that inputs data and allows the taking of measurements from the display of the ultrasound display subsystem, a disk storage device (e.g., hard, floppy, compact disks (CD), digital video discs (DVDs)) for storing the acquired images, and a printer that prints the image from the displayed data. These also have not been shown in FIG. 3 to avoid obscuring the techniques disclosed herein.

Figure 4:
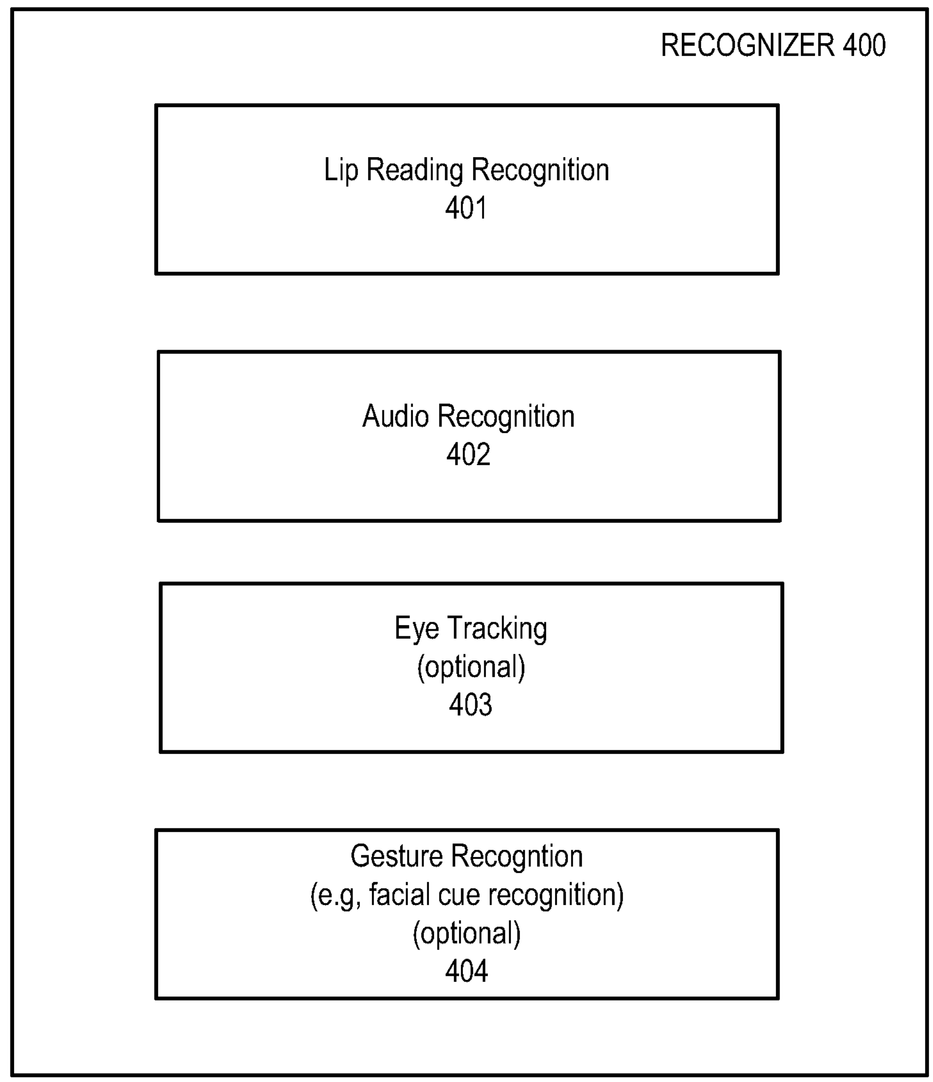
FIG. 4 illustrates a block diagram of one embodiment of a recognizer having one or more recognition components to perform one or more recognition routines.

FIG. 4 illustrates a block diagram of one embodiment of recognizer 400. In one embodiment, recognizer 400 comprises processing logic having hardware (circuitry, dedicated logic, etc.), software (such as is run on a general-purpose computer system or a dedicated machine), firmware, or a combination of the three.

Referring to FIG. 4, recognizer 400 includes lip reading recognition component 401 that performs lip reading recognition in response to lip movements captured by cameras in the ultrasound system.

In one embodiment, recognizer 400 includes audio recognition component 402 that performs audio recognition on audio captured by microphone of the ultrasound system.

Optionally, in one embodiment, recognizer 400 includes eye tracking component 403 that performs eye tracking. In one embodiment, the eye tracking component 403 determines that the user is looking directly at the camera which triggers the lip reading recognition component 401 to operate and perform recognition of lip movements captured by cameras of the ultrasound system.

In another embodiment, recognizer 400 includes gesture recognition component 404 that performs gesture recognition to trigger the operation of lip reading recognition component 401 and/or audio recognition component 402. In one embodiment, gesture recognition component 404 recognizes one or more facial cues to trigger the operation of lip reading recognition component 401. In one embodiment, these facial cues comprise the user closing their eyes for a predetermined period of time, the user winking, the user nodding, or any other predetermined facial movement.

Figure 5:
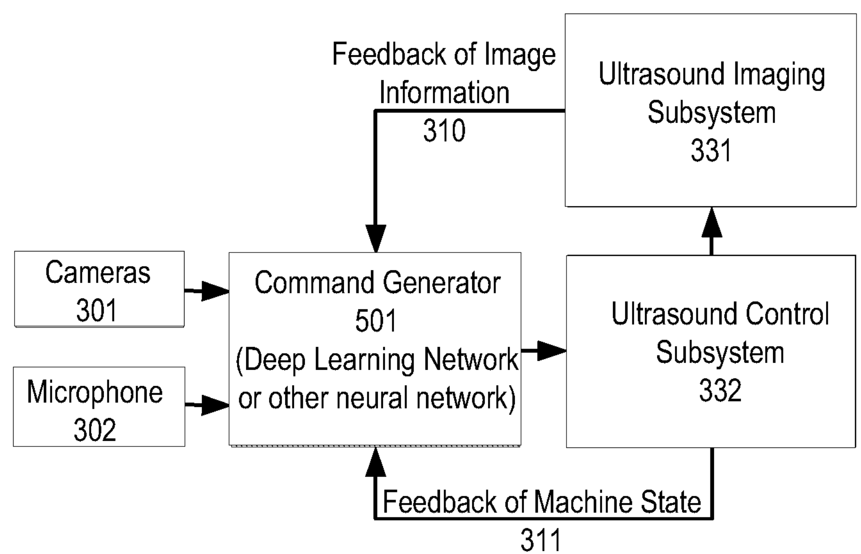
FIG. 5 is a block diagram of an embodiment of an ultrasound system having a command generator that comprises artificial intelligence or machine learning.

FIG. 5 is a block diagram of an embodiment of an ultrasound system having a command generator that comprises artificial intelligence or machine learning. Referring to FIG. 5, only a subset of the components of the ultrasound system of FIG. 3, such as cameras 301, microphone 302, ultrasound imaging subsystem 331 and ultrasound control subsystem 332, are shown to avoid obscuring command generator 501 that uses artificial intelligence or machine learning to generate commands. In one embodiment, the artificial intelligence comprises a neural network, such as, for example, but not limited to, a deep learning neural network.

In one embodiment, command generator 501 receives captured image data from cameras 301, optionally receives capture audio data 302, image information 310 feedback from ultrasound imaging subsystem 331 and machine state information 311 feedback from ultrasound control subsystem 332 and uses the neural network to bias the determination of operations or commands that correlate to the lip movements of the individual using the ultrasound machine.

In one embodiment, command generator 501 generates operations using a deep learning neural network or other neural network. Deep learning is one machine learning technique that employs representation learning methods that allows a machine to be given raw data and determine the representations needed for data classification. Deep learning ascertains structure in data sets using backpropagation algorithms which are used to alter internal parameters (e.g., node weights) of the deep learning machine. Deep learning machines can utilize a variety of multilayer architectures and algorithms to process raw data to identify features of interest without external inputs specifying the features of interest.

Deep learning in a neural network environment includes numerous interconnected nodes referred to as neurons. Upon activation, input neurons activate other neurons based on connections to those other neurons which are governed by the machine parameters. Learning refines these machine parameters as well as the connections between neurons in the network, thereby causing the neural network to behave in a desired manner. In one embodiment, the deep learning network uses a convolutional neural network (CNN) which processes data using convolutional filters to locate and identify learned, observable features in the data. Each filter or layer of the CNN architecture transforms the input data to increase the selectivity and invariance of the data. This abstraction of the data allows the network to focus on the features in the data it is attempting to classify and ignore irrelevant background information.

In one embodiment, the deep learning network uses convolutional neural networks for image analysis as part of recognition for lip reading and/or medical image analysis to identify features of ultrasound images. In one embodiment, the CNN architecture is used for facial recognition in natural images to identify the user of the ultrasound machine for the purpose of eye tracking and determining whether the user is looking at the ultrasound machine as discussed above. In one embodiment, the CNN architecture is also used for audio (e.g., speech) and video (e.g., lip reading) processing.

In one embodiment, the deep learning neural network includes multiple layers which are connected with neural connections. Data flows forward via inputs from the input layer to an output layer and then to an output of the deep learning neural network. The input layer, which includes a plurality of nodes, is followed by one or more hidden layers that include nodes. After the hidden layer(s) is an output layer, which includes at least one node with an output. In one embodiment, each input corresponds to a node of the input layer, and each node of the input layer has a connection to each node of a hidden layer. Each node of one hidden layer has a connection to each node of the next hidden layer, and each node last hidden layer has a connection to the output layer. The output layer has an output to provide an output.

The CNN structure of the deep learning neural network feeds a structure to retain temporary information so that the feature information identified by the CNN architecture is processed as a sequence of information. For example, the lip reading and audio information may include a sequence of information that have different lengths and the information previously identified is used as context information for the current information to enable identification of the user's commands. In one embodiment, the structure includes one or more of a recurrent neural network (RNN), a Long Short-Term Memory (LSTM), and a gated recurrent unit (GRU).

In one embodiment, the nodes are fed with feature data obtained from the lip movements captured by the camera(s) of the ultrasound system.

Certain example connections may be given added weight while other example connections may be given less weight in the neural network. Input nodes are activated through receipt of input data via inputs. Nodes of hidden layers are activated through the forward flow of data through the network via the connections. A node of the output layer is activated after data processed in hidden layers is sent via connections. When the output node of the output layer is activated, the output node outputs an appropriate value based on processing accomplished in hidden layers of the neural network.

In one embodiment, the neural network comprises an image analysis convolutional neural network (CNN), along with a RNN, LSTM, GRU or other such memory-based structure, for lip reading and/or determining one or more features of an ultrasound image. The convolutional neural network receives an input image and generates image features in the form of a vector. A network of LSTMs, RNNs, GRUs or other such structures receives image feature vector from the CNN and produce state and output vectors that are decoded into characters. The characters are used to determine if the lip movements in the images represent a command.

Thus, the use of artificial intelligence, in conjunction with a camera on an ultrasound machine, allows the system to read the lips of the user to determine if the user is giving a command to the ultrasound machine.

In one embodiment, command generator 501 uses the deep learning neural network to generate and cause ultrasound image subsystem 331 to display one or more selectable commands. The selectable commands have associated confidence indication information specifying a level of confidence that each of the one or more commands is the command that is desired. In one embodiment, the confidence indication information comprises a confidence level. Such confidence levels are generated using the neural network in a manner well-known in the art. The confidence levels are affected by the dynamic weighting of different touch inputs used to generate the commands.

In one embodiment, artificial intelligence is not merely determining whether the user is giving a command, but is also used in predicting commands that the user is likely to give the system in the future. Thus, using machine state and image information 310 feedback from the ultrasound imaging subsystem, the neural network of command generator 501 determines operations or biases selection of commands that are generated.

For example, if a nerve in an ultrasound image is not centered in the display screen and a clinician is inserting a needle close to the nerve to inject anesthesia, the neural network recognizes the needle in the image and the examination type as specified in machine state information 311 that is feedback from the ultrasound control system. Once the nerve is identified, the neural network determines or biases the command determination to commands to change the depth and center the nerve in the middle of the display screen, thereby providing ease-of-use in the anesthesiology area. That is, the lip reading command recognition correlates what is displayed in the ultrasound image with what is being recognized through lip reading to bias the command generation process toward commands that change the depth. In this way, knowledge of the workflow is used to improve accuracy of lip reading.

Figure 6:
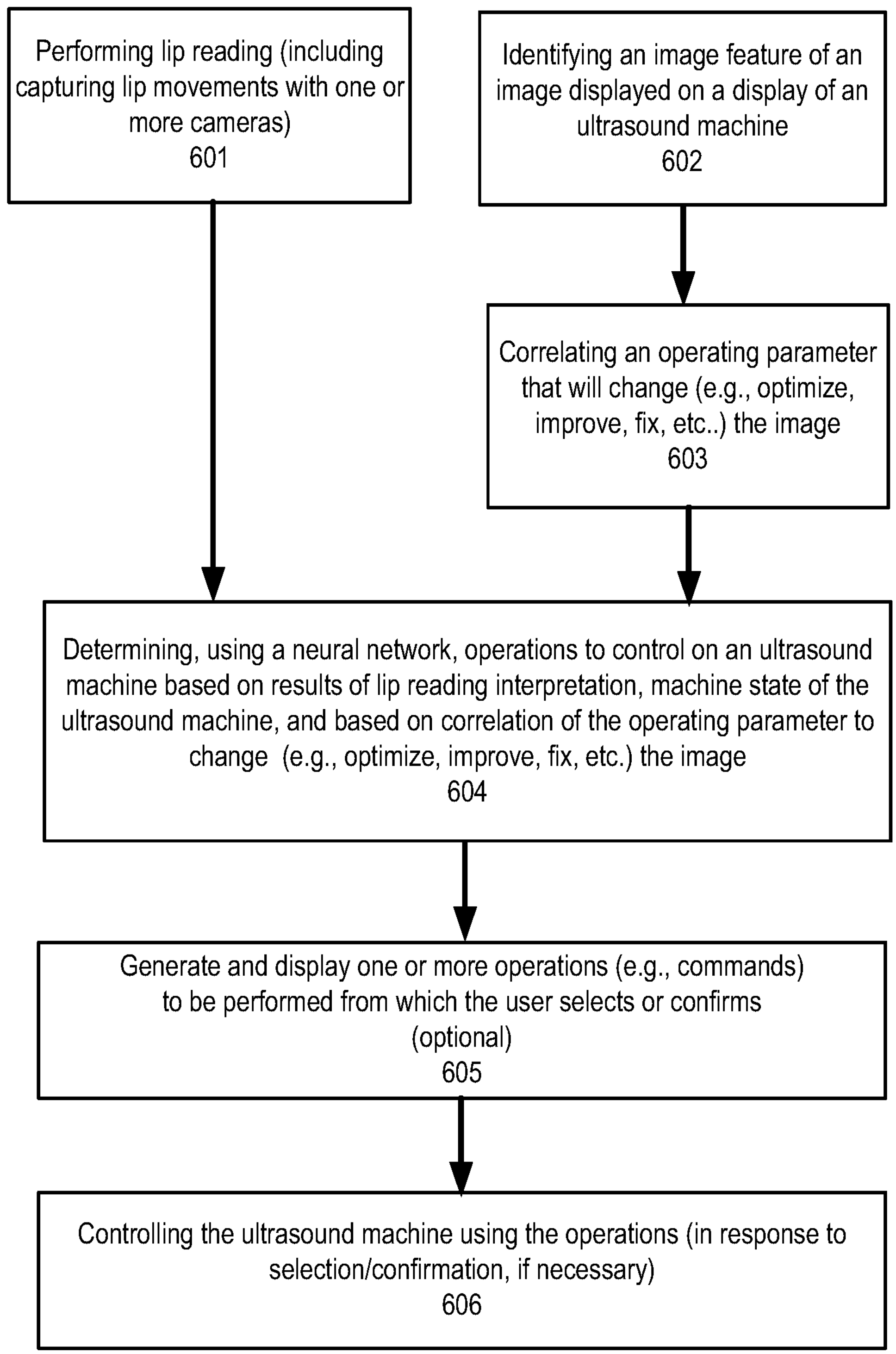
FIG. 6 is a flow diagram of one embodiment of a process for controlling the ultrasound machine using a neural network.

FIG. 6 is a flow diagram of one embodiment of a process for controlling the ultrasound machine using a neural network. In one embodiment, the process is performed by processing logic that includes a neural network that is implemented with processing logic that may comprise hardware (circuitry, dedicated logic, etc.), software (such as is run on a general-purpose computer system or a dedicated machine), firmware, or a combination of the three.

Referring to FIG. 6, the process begins by performing lip reading, including capturing lip movements with one or more cameras and performing recognition on the lip movements (processing block 601).

Processing logic also identifies one or more image characteristics in an image being displayed by the ultrasound imaging subsystem that is not optimized (processing block 602) and correlates an operating parameter that will change the image to help improve, and potentially optimize the image characteristic(s) (processing block 603). This may occur prior to or simultaneously with the lip reading.

In response to performing lip reading and after correlating the operating parameter that will change the image, processing logic uses a neural network (e.g., a deep learning neural network) to determine operations to control the ultrasound machine (processing block 604). The neural network determines the operations based on the results of lip reading recognition, machine state information of the ultrasound machine and based on the correlation of the operating parameter to change the image. In one embodiment, the change of the image is an optimization, improvement, fix or other modification of the image. That is, in one embodiment, the neural network correlates the operating parameter for the optimization, improvement, fix or other modification of the image as part of the process of determining the operation.

In one embodiment, after determining one or more operations based on the results of lip reading recognition, the machine state information of the ultrasound machine, and the correlation of the operating parameter to change the image, processing logic displays one or more user selectable operations that can be performed by the ultrasound machine (processing block 605). Note that this is an optional step and is not required. In an alternative embodiment, a single operation is determined and the command generated for performance by the ultrasound machine without selection or confirmation.

Displaying the operations that have been determined based on the inputs enables the user to select and/or confirm the operation(s) that the ultrasound machine is going to perform, which is advantageous in situations where the command generator cannot ascertain with certainty what operation the user wants performed. This is a confirmation mode.

In one embodiment, the selectable operations are presented on the display of the ultrasound machine under control of the ultrasound imaging subsystem. In one embodiment, the selectable operations are presented in a list according to their likeliness in matching the user's desired operation as determined by the command generator of the ultrasound machine. In one embodiment, the list of selectable operations includes a confidence factor generated by the command generator for each operation or other information to provide the user with an indication of the level of confidence associated with the determination of the operation by the ultrasound machine.

Next, processing logic controls the ultrasound machine using the operations (processing block 606). In one embodiment, the control is in response to a selection and/or confirmation of the operations, if necessary. In one embodiment, the control is performed by the control subsystem of the ultrasound machine.

Note that operations other than those specified in FIG. 6 can be determined and used to control the ultrasound machine, such as those, for example, discussed above.

There is a number of example embodiments described herein.

Example 1 is a method for controlling operation of an ultrasound machine, the method comprising: obtaining one or more touchless inputs; determining one or more operations to control the ultrasound machine based on the one or more touchless inputs and machine state of the ultrasound machine; and controlling the ultrasound machine using at least one of the one or more operations.

Example 2 is the method of example 1 that may optionally include performing lip reading, including capturing lip movements of an individual using at least one camera, and wherein determining the one or more operations to control the ultrasound machine is based on results of performing the lip reading Example 3 is the method of example 1 that may optionally include that determining the one or more operations is further based on ultrasound data.

Example 4 is the method of example 1 that may optionally include that ultrasound data comprises one or more of ultrasound image data, an examination type being performed with the ultrasound machine, and a list of operations being performed with the ultrasound machine.

Example 5 is the method of example 1 that may optionally include that determining the one or more operations is further comprises predicting an operation that the individual is likely to perform based on historical data.

Example 6 is the method of example 1 that may optionally include that determining the one or more operations is further based on captured audio information of the individual and comprises dynamically adjusting, based on an environment in which the ultrasound machine resides, weights associated with results of lip reading recognition and audio recognition to determine the one or more operations to control the ultrasound machine.

Example 7 is the method of example 1 that may optionally include that performing lip reading is triggered in response to determining the individual is looking directly at one camera of the one or more cameras or in response to determining the individual has closed at least one eye for a predetermined period of time, winked, nodded, or performed another facial cue or other gesture.

Example 8 is the method of example 1 that may optionally include identifying one or more image characteristics, and wherein determining the one or more operations is further based on a correlation of an operating parameter to the one or more image characteristics and further wherein controlling the ultrasound machine using the at least one of the one or more operations comprises changing the operating parameter to change an image.

Example 9 is the method of example 1 that may optionally include receiving, at a neural network, one or more of feedback of ultrasound data from an ultrasound imaging subsystem, feedback of machine state from an ultrasound control subsystem, at least one of the one or more touchless inputs, and wherein determining the one or more operations to control the ultrasound machine based on the one or more touchless inputs and the machine state of the ultrasound machine is performed by the neural network.

Example 10 is the method of example 1 that may optionally include that determining one or more operations to control the ultrasound machine comprises generating and displaying one or more selectable commands; capturing information from the individual; and interpreting the captured information as confirming selection of at least one of the one or more selectable commands prior to controlling the ultrasound machine using the at least one operation.

Example 11 is the method of example 1 that may optionally include that the one or more operations comprise at least one selected from a group consisting of adjusting gain, adjusting depth, freezing an image being displayed by the ultrasound machine, saving an image being displayed by the ultrasound machine, adding an annotation at a user-specified location on an image being displayed by the ultrasound machine, and creating a report with one or more images displayed by the ultrasound machine.

Example 12 is the method of example 1 that may optionally include that determining one or more operations to control the ultrasound machine comprises placing an annotation on an image being displayed by the ultrasound machine based on at least one of the one or more touchless inputs.

Example 13 is the method of example 12 that may optionally include that wherein determining one or more operations to control the ultrasound machine further comprises recognizing a start of annotation command, an end of annotation command and one or more annotation movement commands based on at least one touchless input.

Example 14 is the method of example 12 that may optionally include that the one or more annotation movement commands are recognized from eye tracking information.

Example 15 is the method of example 1 that may optionally include identifying the individual from a group of individuals located in proximity to the ultrasound machine based on user identification operation; and providing control of the ultrasound machine through use of touchless inputs to the identified individual.

Example 16 is an apparatus comprising: a display screen; an ultrasound imaging subsystem coupled to the display to generate ultrasound images on the display screen; an ultrasound control subsystem coupled to control the imaging subsystem; one or more cameras to capture images of lip movements of an individual; a microphone to capture audio; a recognizer coupled to the one or more cameras to execute a lip recognition routine on captured images from the one or more cameras to perform lip reading; and a command generator coupled to the recognizer and the control subsystem to determine one or more operations based on one or more touchless inputs from the recognizer and microphone and machine state of the ultrasound machine received from the ultrasound control subsystem and send at least one of the one or more operations to control the ultrasound control subsystem.

Example 17 is the apparatus of example 16 that may optionally include that the command generator comprises a neural network.

Example 18 is the apparatus of example 16 that may optionally include that the command generator is operable to determine the one or more operations based further on ultrasound data.

Example 19 is the apparatus of example 18 that may optionally include that the ultrasound data comprises one or more of ultrasound image data, an examination type being performed with the ultrasound machine, and a list of operations being performed by the ultrasound machine.

Example 20 is the apparatus of example 16 that may optionally include that the command generator is operable to determine the one or more operations by predicting an operation that the individual is likely to perform based on historical data.

Example 21 is the apparatus of example 16 that may optionally include that the command generator is operable to determine the one or more operations based further on captured audio information of the individual and to dynamically adjust, based on an environment in which the ultrasound machine resides, weights associated with results of lip reading recognition and audio recognition to determine the one or more operations to control the ultrasound machine.

Example 22 is the apparatus of example 16 that may optionally include that the recognizer is operable to trigger touchless input control for use by the individual in response to a determination that the individual is looking at one camera of the one or more cameras or in response to a facial cue, wherein the facial cue comprises one of a group consisting of: closing at least one eye for a predetermined period of time, winking, nodding.

Example 23 is the apparatus of example 16 that may optionally include that the command generator comprises a neural network that is operable to receive feedback of ultrasound data from the ultrasound imaging subsystem, feedback of machine state from the ultrasound control subsystem, and at least one of the one or more touchless inputs of the individual from the recognizer, and, in response thereto, the command generator is operable to determine the one or more operations to control the ultrasound control subsystem.

Example 24 is the apparatus of example 16 that may optionally include that the one or more operations comprise at least one selected from a group consisting of adjusting gain, adjusting depth, freezing an image being displayed by the ultrasound machine, saving an image being displayed by the ultrasound imaging subsystem, adding an annotation at a user-specified location on an image being displayed by the ultrasound imaging subsystem, and creating a report with one or more images displayed by the ultrasound imaging subsystem.

Example 25 is the apparatus of example 16 that may optionally include that the one or more operations comprise placing an annotation on an image being displayed by the ultrasound imaging subsystem based on the one or more touchless inputs, including recognizing a start of annotation command, an end of annotation command and one or more annotation movement commands based on information captured from the individual.

Example 26 is an article of manufacture having one or more computer readable storage media storing instructions thereon which, when executed by a system, cause the system to perform a method for controlling operation of an ultrasound machine, where the method comprises: obtaining one or more touchless inputs; determining one or more operations to control the ultrasound machine based on the one or more touchless inputs and machine state of the ultrasound machine; and controlling the ultrasound machine using at least one of the one or more operations.

Some portions of the detailed descriptions above are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The algorithms and displays presented herein are not inherently related to any particular computer or other apparatus. Various general-purpose systems may be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the invention as described herein.

A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; etc.

Whereas many alterations and modifications of the present invention will no doubt become apparent to a person of ordinary skill in the art after having read the foregoing description, it is to be understood that any particular embodiment shown and described by way of illustration is in no way intended to be considered limiting. Therefore, references to details of various embodiments are not intended to limit the scope of the claims which in themselves recite only those features regarded as essential to the invention.

I claim:

1. A system for controlling an ultrasound machine, the system comprising:

one or more sensors to receive at least one touchless input;

an ultrasound control subsystem to generate machine state information of the ultrasound machine; and a neural network to determine, based on the at least one touchless input and the machine state information, one or more operations to control the ultrasound machine.

2. The system as described in claim 1, further comprising a command generator to control the ultrasound machine using at least one of the one or more operations.

3. The system as described in claim 2, wherein at least one of the one or more sensors is implemented to receive an additional touchless input that indicates a selection of the at least one of the one or more operations.

4. The system as described in claim 1, wherein the machine state information includes historical data that indicates a user action.

5. The system as described in claim 4, wherein the user action includes a multi-user action.

6. The system as described in claim 1, wherein the machine state information indicates a type of examination being performed with the ultrasound machine.

7. The system as described in claim 1, further comprising:

an ultrasound imaging subsystem to generate image information corresponding to an ultrasound image; and a command generator to determine at least one of the one or more operations for the controlling the ultrasound machine based on the image information.

8. The system as described in claim 1, further comprising a recognizer component implemented to enable an activation mode for enabling the controlling the ultrasound machine, wherein:

at least one of the one or more sensors is implemented to receive an additional touchless input that represents a request for enabling the activation mode;

the recognizer component is implemented to enable the activation mode responsive to the at least one of the one or more sensors receiving the additional touchless input; and the neural network is implemented to determine the one or more operations to control the ultrasound machine responsive to the recognizer component enabling the activation mode.

9. A method for controlling an ultrasound machine, the method comprising:

receiving one or more touchless inputs;

determining a machine state of the ultrasound machine; and determining one or more operations for controlling the ultrasound machine including placing, based on the one or more touchless inputs and the machine state, an annotation on an ultrasound image that is displayed by the ultrasound machine.

10. The method as described in claim 9, further comprising generating, based on the one or more touchless inputs, the annotation.

11. The method as described in claim 9, wherein the one or more touchless inputs indicate the annotation.

12. The method as described in claim 9, further comprising determining a start and a stop of the annotation based on a start command and a stop command, respectively, included in the one or more touchless inputs.

13. The method as described in claim 9, further comprising:

receiving at least one additional touchless input that indicates a movement command; and moving, based on the at least one additional touchless input, the annotation on the ultrasound image.

14. The method as described in claim 13, wherein the movement command indicates a direction to move the annotation on the ultrasound image.

15. The method as described in claim 13, wherein the at least one additional touchless input includes an eye movement to indicate the movement command.

16. A method comprising:

identifying an individual from a group of individuals located in proximity to an ultrasound machine;

determining a machine state of the ultrasound machine; and providing control of the ultrasound machine to the individual through use of touchless inputs, the providing including:

receiving at least one touchless input from the individual;

determining, based on the at least one touchless input and the machine state, one or more operations for the control of the ultrasound machine; and controlling the ultrasound machine using at least one of the one or more operations.

17. The method as described in claim 16, wherein the identifying is based on at least one of a direction of eye glance of the individual or a gesture performed by the individual.

18. The method as described in claim 16, further comprising obtaining examination data, wherein the identifying is based on information in the examination data that identifies the individual as performing an ultrasound examination with the ultrasound machine.

19. The method as described in claim 16, wherein the providing includes not accepting additional touchless inputs from additional individuals in the group of individuals.

20. The method as described in claim 16, further comprising setting one or more configuration parameters based on the individual, wherein the controlling is based on the one or more configuration parameters.

* * * * *